(12) United States Patent
Seidling et al.

(10) Patent No.: US 8,333,954 B2
(45) Date of Patent: Dec. 18, 2012

(54) FOAMABLE SANITIZING COMPOSITIONS

(75) Inventors: Jeffery R. Seidling, Neenah, WI (US);
Corey Thomas Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1391 days.

(21) Appl. No.: 11/799,042

(22) Filed: Apr. 30, 2007

(65) Prior Publication Data

US 2009/0098067 A1    Apr. 16, 2009

(51) Int. Cl.
*A61K 8/00* (2006.01)
*A61K 8/18* (2006.01)
*A61K 31/045* (2006.01)
*A01N 31/00* (2006.01)
*A61Q 17/04* (2006.01)

(52) U.S. Cl. .......................................... 424/59; 514/724

(58) Field of Classification Search .................. None
See application file for complete search history.

(56) References Cited

U.S. PATENT DOCUMENTS

| | | | | |
|---|---|---|---|---|
| 5,607,980 A * | 3/1997 | McAtee et al. | ............... | 514/476 |
| 5,635,469 A * | 6/1997 | Fowler et al. | ............... | 510/406 |
| 5,834,516 A * | 11/1998 | O'Lenick, Jr. | ............... | 514/563 |
| 6,039,965 A * | 3/2000 | Donlan et al. | ............... | 424/405 |
| 6,053,364 A | 4/2000 | Van der Heijden | | |
| 6,183,766 B1 * | 2/2001 | Sine et al. | ............... | 424/405 |
| 6,290,104 B1 | 9/2001 | Bougamont | | |
| 6,383,997 B1 * | 5/2002 | McManus | ............... | 510/131 |
| 6,423,329 B1 | 7/2002 | Sine et al. | | |
| 6,536,629 B2 | 3/2003 | Van der Heijden | | |
| 2005/0129626 A1 | 6/2005 | Koivisto | | |
| 2006/0182690 A1 | 8/2006 | Veeger et al. | | |
| 2007/0065383 A1 | 3/2007 | Fernandez de Castro | | |

FOREIGN PATENT DOCUMENTS

| | | |
|---|---|---|
| EP | 0121791 A2 | 10/1984 |
| EP | 1811013 A1 | 7/2007 |
| WO | WO 2006094387 A1 | 9/2006 |

OTHER PUBLICATIONS

PCT International Search Report for International Application No. PCT/IB2008/050803 dated Jul. 2, 2008.
Myers, Drew. *Surfaces, Interfaces, and Colloids Principles and Applications*, 2$^{nd}$ Edition., p. 12.9, New York: Wiley & Sons Inc., 1999.
Schütz, F. *Some Physiological Applications of Measurements of Foam Time*, Pharmacological Laboratories, College of Pharmaceutical Society, University of London, and the Medical School, Hospitals Centre, University of Birmingham, Jan. 22, 1943.

* cited by examiner

*Primary Examiner* — Fereydoun G Sajjadi
*Assistant Examiner* — David Browe
(74) *Attorney, Agent, or Firm* — Dority & Manning, P.A.

(57) ABSTRACT

Foamable sanitizing compositions are disclosed. The compositions contain alcohol, water, a foaming agent, and a foam strengthening agent. The foaming agent which may comprise a derivatized dimethicone has been found to cause the alcohol solution to foam even though alcohol has various defoaming properties. The foam strengthening agent may comprise, for instance, a betaine that contains organic molecules wherein at least 90% of the organic molecules have a carbon chain length of 18 carbon atoms or greater. In one embodiment, the composition can be contained in a non-aerosol dispensing container that mixes the composition with air causing the composition to foam when dispensed.

14 Claims, 1 Drawing Sheet

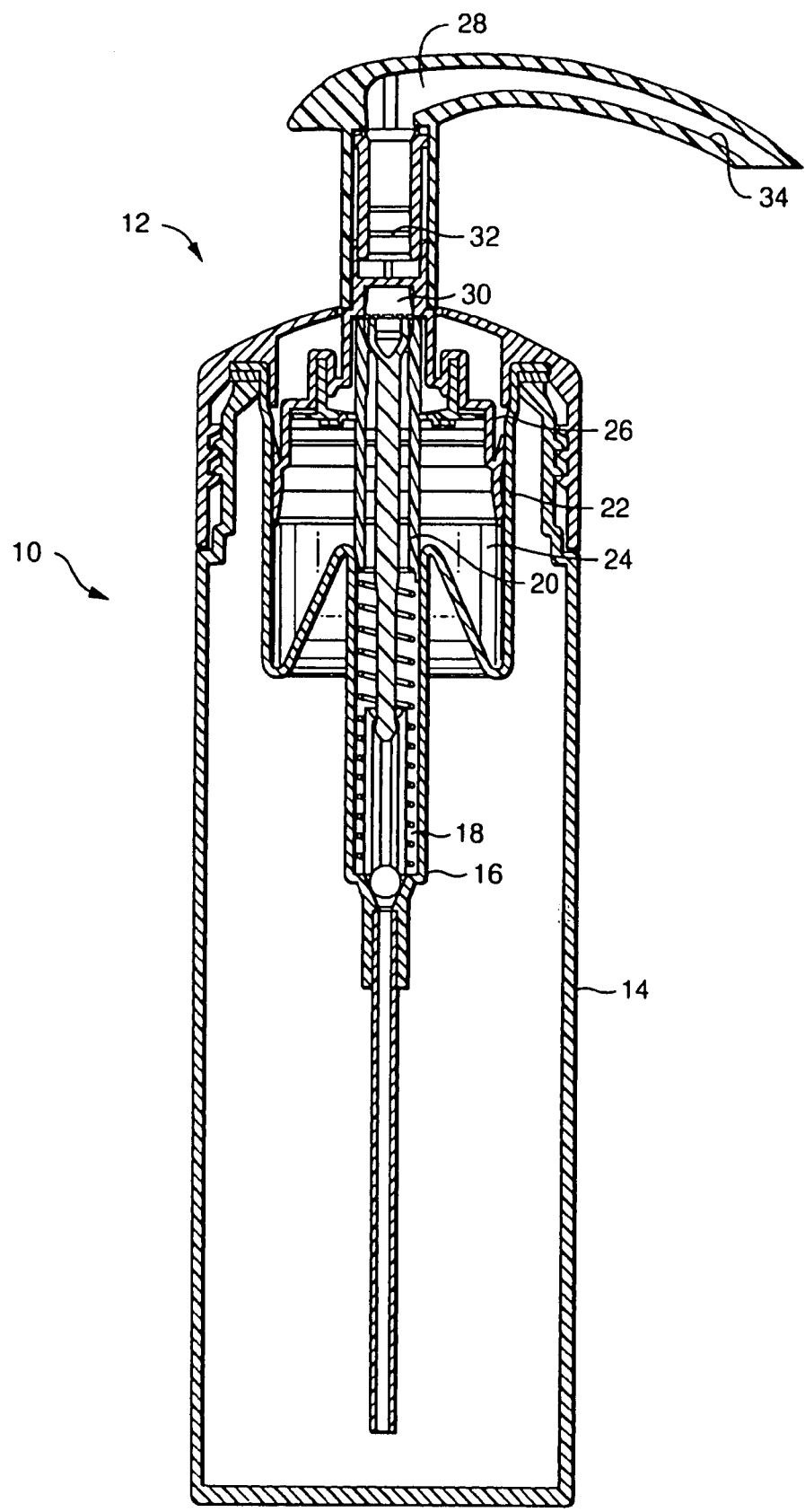

FOAMABLE SANITIZING COMPOSITIONS

BACKGROUND

Conventional hand cleansing formulations contain solvents and/or surfactants capable of solubilizing or emulsifying soils present on the skin's surface. The cleaning products may come in the form of, for instance, a bar soap which produces a lather or foam by agitation with the hands in the presence of water or a gel that may be, for instance, pumped from a dispenser.

Recently, consumer foamable cleansers have appeared on the market. Foamable cleansers are typically kept in a dispensing container that mixes the cleansing composition with air when dispensed immediately forming a foam or lather. These types of products have been used extensively in the medical field by doctors and other medical personnel. Compositions dispensed as foams have been regarded as desirable in part because of an association of foam with cleaning ability.

The liquid-gas foams are composed of gas cells surrounded by a liquid. The gas cells consist of films of liquid (lamellae) surrounding the gas bubble with the planar faces of liquid films meeting at angular intersections called Plateau junctions. To be mechanically stable, the lamellae of three bubbles meeting must be at an angle of 120°. With the addition of more bubbles to the foam, the perfect angle for mechanical stability is lost and the bubbles take on a more polygonal type of network. In a three dimensional gas cell within a foam, the resulting cell is polyhedral in nature.

A liquid-gas foam can be considered an emulsion with the liquid being the continuous phase and the dispersed phase composed of gas bubbles. Surfactants are frequently used to form most foams. The surfactants reduce the surface tension of the liquid phase and stabilize the films against rupture. The polar heads of the surfactants arrange themselves within the polar liquid and the hydrophobic tails project out into the air if the bubble is on the outside of the film, or into the Plateau junction if the bubble is within the film.

Liquid-gas foams can be categorized into dry and wet foams. In a dry foam, there is very little liquid (less than 1% by volume) and it exists in very thin films. The junctions of these films can be visualized in terms of a thin line with no discernable width. The polyhedral nature of the gas cell is clearly visible and very little fluid is maintained within the foam making this foam fairly stable.

A foam containing a percent or more of liquid is considered a wet foam. Liquid accumulates in the Plateau borders of these foams causing them to increase in width. Due to the swelling of the Plateau junctions, the corners and edges of the polyhedral cell are rounded off. Pressure differences between adjacent cells and gravity force liquid from these foams passing the liquid through the Plateau junctions (drainage) to the substrate until the lower-energy dry foam is reached or the bubble ruptures. However, with increased liquid, the cells regain their spherical nature and the foam degrades into a bubbly liquid.

For a liquid to foam with any degree of success, it must be able to expand its surface area to form a membrane around gas bubbles, possess the correct rheological and surface properties to reduce the thinning of the lamellae leading to bubble coalescence, and slow the diffusion of gas across lamellae from small to large bubbles or to the surrounding atmosphere.

One problem that has been experienced in the past in formulating foamable cleansers is the ability to incorporate an alcohol into the compositions. Alcohols, for instance, have very effective sanitizing properties. Alcohols, however, are also known defoaming agents making their incorporation into foamable cleansers somewhat problematic. For example, alcohols reduce the surface tension of water in surfactant/water solutions below that needed to maintain the integrity of the lamellae of the foam bubble. Alcohols also displace surfactant molecules at the air/water interface disrupting the stabilization of any foam being formed and causing collapse.

As a consequence, in the past, foamable hand sanitizers containing alcohols have been placed in aerosol containers that produce a pressure high enough to generate a foam. Alternatively, alcohols have been combined with expensive or complicated ingredients in order to facilitate formation of a foam. For instance, those skilled in the art have proposed in the past adding fluorinated surfactants, such as a perfluoroalkylethyl phosphate, to sanitizing compositions containing alcohol.

In view of the above, a need currently exists for an improved foamable cleansing composition that contains a sanitizer. In particular, a need exists for a foamable sanitizing composition that contains an alcohol sanitizer.

SUMMARY

In general, the present disclosure is directed to foamable sanitizing compositions. For example, in one embodiment, the sanitizing composition contains an alcohol in an amount of at least about 20 percent by weight, such as from about 30 percent to about 90 percent by weight, such as from about 40 percent to about 70 percent by weight. In general, any suitable alcohol may be used that has sanitizing properties. The alcohol may comprise, for instance, ethanol, isopropyl alcohol and the like. In accordance with the present disclosure, in order to make the sanitizing composition foamable, the alcohol is combined with a foaming agent such as at least one derivatized dimethicone and a foam strengthening agent. The foam strengthening agent, for instance, can comprise an amphoteric surfactant or a zwitterionic surfactant containing organic molecules in which at least 90% of the molecules have a carbon chain length of 18 carbon atoms or greater. In one embodiment, for instance, the foam strengthening agent may comprise a betaine. The foam strengthening agent increases foam longevity and stability.

The foaming agent and the foam strengthening agent are capable of causing the composition to foam when the composition is combined with air using, for instance, a manual pump dispenser. Although the sanitizing composition may be dispensed from an aerosol container, an aerosol is not needed in order to cause the composition to foam. Also of particular advantage, the sanitizing composition is foamable without having to include fluorinated surfactants.

Various different derivatized dimethicone foaming agents may be used in the composition of the present disclosure. The derivatized dimethicone, for instance, may comprise a dimethicone copolyol, such as an ethoxylated dimethicone. In one embodiment, the derivatized dimethicone is linear, although branched dimethicones may be used.

Particular examples of dimethicone copolyols that may be used include polyoxyethylene glycol dimethicone containing from about 5 to about 20 moles of polyoxyethylene glycol. The derivatized dimethicone may be, for instance, PEG-10 dimethicone, PEG-12 dimethicone, or mixtures thereof.

In one embodiment, the derivatized dimethicone may comprise a dimethicone copolyol ester. An example, for instance, of a dimethicone copolyol ester is dimethicone PEG-7 cocoate.

The derivatized dimethicone may be present in the sanitizing composition in an amount sufficient to cause the composition to foam when combined with air. For instance, the derivatized dimethicone may be present in the composition in an amount from about 0.5 percent to about 15 percent by weight, such as from about 4 percent to about 10 percent by weight.

The foam strengthening agent, on the other hand, may be present in the composition in an amount from about 0.1% by weight to 10% by weight or greater. In one embodiment, for instance, the foam strengthening agent may be present in the composition in an amount from about 0.2% by weight to about 5% by weight.

In one embodiment, the foamable sanitizing composition as described above is dispensed from a dispensing container. The dispensing container may include a non-aerosol pumping device configured to combine the sanitizing composition with air. For instance, the pumping device may include an air pump and a liquid pump that are both in communication with an actuating head. Displacing the actuating head manually causes the air pump to pump air and the liquid pump to pump the sanitizing composition into a mixing chamber for forming a foam as the composition is dispensed.

Other features and aspects of the present disclosure are discussed in greater detail below.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the following figures:

FIG. 1 is a cross-sectional view of one embodiment of a dispensing container that may be used in accordance with the present disclosure.

Repeat use of reference characters in the present specification and drawings is intended to represent same or analogous features or elements of the disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a foamable sanitizing composition. The composition, for instance, can contain an alcohol in an amount sufficient to provide the composition with antimicrobial properties. In particular, the alcohol can be present in an amount sufficient to destroy potentially harmful microorganisms.

In accordance with the present disclosure, the alcohol is combined with a foaming agent comprising a derivatized dimethicone. In addition, the composition can also contain a foam strengthening agent which may comprise, for instance, an amphoteric or zwitterionic surfactant. The present inventors have discovered that the foaming agent and foam strengthening agent can overcome the de-foaming properties of the alcohol and can cause the composition to foam when aerated. Of particular advantage, the foaming agent and foam strengthening agent can make a composition containing substantial amounts of an alcohol foam without the necessity of using complex chemistries. For instance, the sanitizing compositions can be foamable without the addition of any fluorinated surfactants.

Foamable sanitizing compositions made in accordance with the present disclosure can be used in various different applications and for various different purposes. For example, in one embodiment, the sanitizing composition can be formulated for use by medical personnel to disinfect their hands. In addition, the sanitizing composition of the present disclosure can be used by consumers for everyday use. For example, the foamable sanitizing composition can be used to sanitize ones hands at home or at the office.

The sanitizing composition of the present disclosure is also well suited for use by toddlers. In particular, the foamable composition may be used by parents, teachers and other caregivers for teaching proper hand hygiene to toddlers. The foaming action of the sanitizing composition makes the experience fun and interactive for the toddlers and increases the likelihood that the toddlers will want to repeat the experience without being told or instructed.

As described above, the sanitizing composition of the present disclosure generally contains an alcohol in combination with the foaming agent and foam strengthening agent. In general, any suitable alcohol having sanitizing properties can be used. For instance, the alcohol may contain from about 1 to about 4 carbon atoms in the carbon chain. Examples of suitable alcohols include, for instance, 2-propanol or n-propanol. In one embodiment, the alcohol may comprise ethanol.

The amount of alcohol contained within the sanitizing composition may depend upon various factors. For instance, the amount of alcohol contained in the composition may depend upon the desired use for the composition. In general, an alcohol is present in the composition in an amount of at least 20 percent by weight. For instance, the alcohol can be present in the composition in an amount from about 30 percent to about 90 percent by weight, such as from about 40 percent to about 70 percent by weight. Of particular advantage, even at the higher weight percentages, the composition can still remain foamable due to the presence of the derivatized dimethicone.

Derivatized dimethicones that may be used in the present disclosure include dimethicone copolyols and dimethicone copolyol esters, including ethoxylated dimethicones. Dimethicone copolyols generally include a dimethicone backbone with unprotected ethylene oxide pendant groups. The molecules can exist as multi-pendant or linear dimethicone copolyols. A linear dimethicone copolyol is as follows:

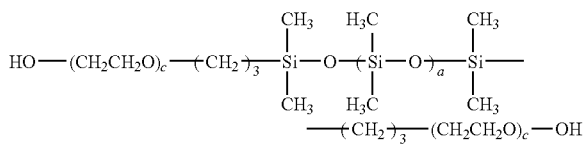

wherein A is from 1 to about 2000 and C is from 1 to about 30. A multi-pendant dimethicone copolyol is as follows:

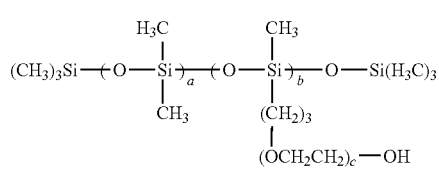

wherein A is from 1 to about 2000, B is from about 1 to about 20, and C is from about 1 to about 30.

Although multi-pendant dimethicone copolyols may be desirable in some applications, linear dimethicone copolyols have thus far shown better foaming properties. Although unknown, it is believed that the linear molecules include polar ethylene oxide branches that can more readily participate in hydrogen bonding between the alcohol and other components contained within the composition. Thus, the linear molecules are capable of stabilizing individual bubbles within the foam. In addition, the linear nature of the molecules may form bridges between bubbles with one polar end inserted into the lamella of one bubble, the silicone backbone in the plateau junction and the other polar end inserted into the lamella of an adjacent bubble within the foam. Further, the silicone-silicone interactions in linear molecules may also contribute to a cross-linked network within and in between films adding excellent stability to the foam and an increase in the quality and quantity of foam generated when the composition is aerated. Multi-pendant dimethicone copolyols are also well suited to stabilizing single bubbles as described above.

Dimethicone copolyols that may be used in the composition of the present disclosure include, in one embodiment, for instance, polyoxyethylene glycol dimethicones containing from about 2 moles of polyoxyethylene glycol to about 40 moles of polyoxyethylene glycol, such as containing from about 5 moles of polyoxyethylene glycol to about 20 moles of polyoxyethylene glycol. Particular examples of dimethicone copolyols that are well suited for use in the composition of the present disclosure include PEG-8 dimethicone, PEG-10 dimethicone, PEG-12 dimethicone, and mixtures thereof. In one particular embodiment, for instance, PEG-10 dimethicone may be mixed with PEG-12 dimethicone.

Dimethicone copolyol esters, on the other hand, generally include a dimethicone backbone with ethylene oxide pendant groups end-blocked with a fatty acid derivative. For instance, the structure of a dimethicone copolyol ester is as follows:

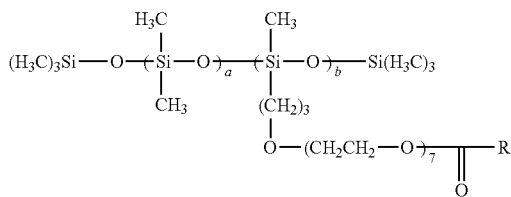

wherein R is derived from a fatty acid, A is from about 1 to about 2000 and B is from about 1 to about 30.

Fatty acids that may be used to form the dimethicone copolyol ester include fatty acids having a carbon chain from about 6 carbon atoms to about 30 carbon atoms. The fatty acid, for instance, may be derived from avocado, olive, coconut, soybean, and the like. Particular fatty acids that may be present in the dimethicone copolyol ester include decanoic acid, lauric acid, dodecanoic acid, palmitic acid, myristic acid, stearic acid, oleic acid, and mixtures thereof.

In the above formula, the dimethicone copolyol ester is shown containing 7 moles of polyoxyethylene glycol. It should be understood, however, that the dimethicone copolyol ester may contain more or less polyoxyethylene glycol. For instance, the ester may contain from about 2 moles to about 20 moles of PEG. The ethylene oxide pendant group is polar in nature and allows for hydrogen bonding with water and alcohol molecules that may be within the composition. The fatty acid chain can participate in hydrophobic interactions with other components in the composition to add stability. The siloxane backbone, on the other hand, can participate in silicone-silicone interactions to further stabilize the foam.

The amount of derivatized dimethicone present within the sanitizing composition can depend upon various factors including the amount of alcohol contained in the composition, the desired result, the manner in which the composition is to be dispensed, and the end use application for the composition. In general, for instance, the composition can contain the derivatized dimethicone in an amount from about 0.5 percent to about 15 percent by weight, such as from about 4 percent to about 10 percent by weight. In one embodiment, the composition contains the derivatized dimethicone in an amount greater than about 5 percent by weight, such as in an amount greater than about 6 percent by weight.

The particular type of derivatized dimethicone added to the sanitizing composition can also vary depending upon the other ingredients present in the composition. For instance, at lower alcohol levels, dimethicone copolyol esters may be preferred. For instance, dimethicone copolyol esters are particularly well suited for inclusion into compositions containing less than about 40% by weight alcohol, such as less than about 20% by weight alcohol.

Dimethicone copolyols, on the other hand, are well suited for inclusion into compositions containing greater amounts of alcohol. For example, dimethicone copolyols are well suited for use in sanitizing compositions containing an alcohol in amounts greater than about 40% by weight. It should be understood, however, that dimethicone copolyols also are well suited for use in compositions containing alcohols in lesser amounts than described above. For example, in still other embodiments, it may be desirable to combine a dimethicone copolyol with a dimethicone copolyol ester.

In addition to an alcohol and a foaming agent, the composition can also contain a foam strengthening agent. The foam strengthening agent can be added to the composition in order to increase foam longevity. In particular, the foam strengthening agent increases the stability of the foam and makes the foam more resistant to compressive forces. The foam strengthening agent can be, for instance, an amphoteric or zwitterionic surfactant, such as a betaine. More particularly, the foam strengthening agent contains surfactant molecules wherein greater than 90% of the molecules have a hydrophobic carbon chain length of 18 carbon atoms or greater, such as 20 carbon atoms or greater.

Examples of foam strengthening agents that may be used include meadowfoamamidopropyl betaine, canolamidopropyl betaine, behenamidopropyl betaine, behenyl betaine, dimer dilinoleamidopropyl betaine, almondamidopropyl betaine, cupuassuamidopropyl betaine, isostearamidopropyl betaine, oleamidopropyl betaine, oleylamidopropyl betaine, olivamidopropyl betaine, ricinoleamidopropyl betaine, sesamidopropyl betaine, soyamidopropyl betaine, stearamidopropyl betaine, steryl betaine, olivamidopropyl betaine and mixtures thereof, other surfactants made from rapeseed oil, the fatty acid portions of carnuba wax and candelilla wax, borage seed oil, linseed oil, castor oil, veronia oil, tung oil, jojoba oil, ongonkea oil, or tall oil may also be used.

In one particular embodiment, for instance, the foam strengthening agent comprises meadowfoamamidopropyl betaine. Meadowfoamamidopropyl betaine is commercially available from the Fanning Corporation.

The amount of foam strengthening agent present in the composition can depend upon various factors and the desired result. In general, foam strengthening agent can be present in an amount from about 0.01% to about 10% by weight, such as from about 0.1% to about 5% by weight, such as from about 0.1% to about 2% by weight.

The sanitizing composition can also include water. The amount of water present in the composition may vary depending upon the particular application and the desired result. Water is generally present in the composition in an amount of at least 10 percent by weight, such as from about 20 percent to about 75 percent by weight. In one particular embodiment, for instance, water may be present in an amount from about 25 percent to about 60 percent by weight.

The sanitizing composition of the present disclosure may contain various other ingredients to impart desired characteristics to the composition. Examples of additives that may be added to the composition include detackifiers, fragrances, thickeners, emollients, suspended beads, organic sunscreens, dyes, preservatives, and the like.

Thickeners that may be used in the composition include various modified celluloses. For instance, the thickener may comprise ethyl cellulose, hydroxypropyl cellulose, carboxymethyl cellulose, hydroxypropyl methyl cellulose, hydroxyethyl methyl cellulose, and combinations thereof. Other thickeners include natural gums, such as guar gum, carrageenan, gum Arabic, locust bean gum, xanthan gum, and mixtures thereof. Other various polymeric thickeners that may be used include a hydroxyethyl cellulose, a polyether propanoic acid TMX copolymer or an acrylate polymer such as an alkyl acrylate crosspolymer containing from about 10 carbon atoms to about 30 carbon atoms in the alkyl chain.

The sanitizing composition can also contain various emollients. Particular emollients that may be used include ethoxylated and propoxylated alcohols, such as ethoxylated or propoxylated cetyl alcohols and ethoxylated lanolin.

Organic sunscreens that may be present in the composition include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

The sanitizing composition can also contain various preservatives to increase the shelf life of the composition. Some suitable preservatives that can be used in the present disclosure include, but are not limited to, Kathon CG®, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); EDTA and salts thereof; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; imidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

The amount of the preservative utilized in the cleansing composition can generally vary depending on the relative amounts of the other components present within the formulation. For example, in some embodiments, the preservative is present in the formulation in an amount between about 0.001% to about 5% by weight, in some embodiments between about 0.001 to about 1% by weight, and in some embodiments, between about 0.1% to about 0.15% by weight of the formulation.

Still other optional ingredients that may be included in the sanitizing composition include, but are not limited to, anti-microbial agents, antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); hydrotropes (helps dissolve some anti-microbial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); natural moisturizing factors, amino acids, and the like.

The sanitizing composition may be prepared in any conventional manner, e.g. by simply admixture of the components. For instance, in one embodiment, all of the ingredients can be added and mixed together at the same time.

The sanitizing composition is foamable in that the composition is specifically formulated to form a foam when aerated. For example, in one embodiment, the composition may be contained in an aerosol container. In an aerosol container, the composition is maintained under pressure sufficient to cause foam formation when dispensed.

Of particular advantage, however, the sanitizing composition of the present disclosure is foamable without the necessity of being placed in an aerosol container. For instance, in an alternative embodiment, the composition may be contained in a manual dispensing foam pump container. The non-aerosol container, for instance, may entrain air in the foamable composition as it is dispensed.

For instance, referring to FIG. 1, one embodiment of a dispensing container generally 10 that may be used with the sanitizing composition is illustrated. The dispensing container 10 includes a dispensing assembly 12 that is screwed onto a liquid container 14. The dispensing assembly 12 includes a liquid pump 16 that comprises a liquid pump chamber 18 and a liquid pump piston 20. The dispensing container further includes an air pump 22 with an air pump chamber 24 and an air pump piston 26. The liquid piston 20 and the air piston 26 are coupled to an actuating head 28.

In order to dispense a foam from the dispensing container 10, the actuating head 28 is displaced by being pressed downwardly causing the pistons 20 and 26 to move downwards as well. As the pistons 20 and 26 are moved downwards, the volumes of the chambers 18 and 24 are reduced causing air and liquid to enter a mixing chamber 30. The liquid and air mixture then passes through a screen or mesh 32 and into a dispenser 34.

After foam is dispensed through the dispenser 34, the actuating head 28 is released and thus returns to its initial position.

The present disclosure may be better understood with respect to the following examples.

EXAMPLE 1

The following tests were performed in order to observe the foaming ability of various different foaming agents when contained in a 70 percent ethanol solution.

A 70 percent ethanol solution was first prepared containing 190 proof alcohol combined with water. Six percent by weight of the foaming agents listed in the table below were then combined with the alcohol solution. The solution was mixed at room temperature until homogeneous.

Foaming was determined by passing the resulting solution through an AIRSPRAY M3 mini-foamer. After priming the pump contained in the dispensing container, two pumps of formulation were dispensed into a beaker. Foam generation was visually confirmed following dispension.

The quality of the foam produced was visually inspected over a 30 minute period. Drainage is an indicator of foam stability. If a tight, cohesive foam was generated and its integrity was maintained with very little drainage over a period of 30 seconds, the foam was given a rating of 1. If a tight, cohesive foam was generated and slow drainage of the foam caused it to degrade during the 30 second time period, the foam was given a rating of 2. If a foam was generated but degraded nearly immediately, the foam was rated a 3. If a non-cohesive bubbly liquid was generated, the foam was rated a 4.

The following results were obtained:

| Trade Name | Supplier | Chemical Name | Solubility | Foam | Quality of Foam |
|---|---|---|---|---|---|
| GE SM2115 | GE Specialty Silicones | Amodimethicone, Isolaureth-6, Glycerin, Octoxynol-40 | Y | N | — |
| Eumulgin HPS | Cognis Corp. | Coceth-7, PPG-1-PEG-9 Lauryl Glycol Ether, PEG-40 Hydrogenated Castor Oil | Y | N | — |
| MackproPlus Rice-C | McIntyre Group LTD | Cocodimonium Hydroxypropyl Hydrolyzed Rice Protein | Y | N | — |
| MackproPlus Silk-C | McIntyre Group LTD | Cocodimonium Hydroxypropyl Hydrolyzed Silk Protein | Y | N | — |
| MackproPlus Soy-C | McIntyre Group LTD | Cocodimonium Hydroxypropyl Hydrolyzed Soy Protein | Y | N | — |
| MackproPlus Wheat-C | McIntyre Group LTD | Cocodimonium Hydroxypropyl Hydrolyzed Wheat Protein | Y | N | — |
| Silsense DW-AV | Noveon | Dimethicone PEG-7 Avacadoate | Y | Y | 4 |
| Silsense SW-12 | Noveon | Dimethicone PEG-7 Cocoate | Y | Y | 4 |
| Silsense DW-O | Noveon | Dimethicone PEG-7 Olivate | Y | Y | 4 |
| ABIL B 9950 | Degussa | Dimethicone Propyl PG-Betaine | Y | N | — |
| Varisoft PATC | Degussa | Palmitamidopropyltrimonium Chloride | Y | N | — |
| KR-945A | Shin Etsu | PEG-3 Dimethicone | Y | N | — |
| Silsoft 805 Dimethicone | GE Advanced Materials Silicones | PEG-8 Dimethicone | Y | Y | 4 |
| Silsurf Di1010 | Siltech LLC | PEG-10 Dimethicone | Y | Y | 1 |
| Dow Corning 5329 fluid | Dow Corning | PEG-12 Dimethicone | Y | Y | 1 |
| ABIL B 8843 | Degussa | PEG-14 Dimethicone | Y | Y | 4 |
| DC 3-3009 Fluid | Dow Corning | PEG-12 Dimethicone Crosspolymer, Dimethicone, Cyclopentasiloxane | Partially | N | — |
| Silsoft 440 | GE Advanced Materials Silicones | PEG-20/PPG-23 Dimethicone | Y | Y | 4 |
| Silsoft 920 | GE Advanced Materials Silicones | PEG-12 Dimethicone | Y | Y | 4 |
| Antil 127 | Degussa | PEG-120 Methyl Glucose Dioleate | Y | N | — |
| Crovol PK-70 | Croda | PEG-45 Palm Kernel Glycerides | Y | N | — |
| Carbowax PEG 200 | Dow Chemical | PEG4 | Y | N | — |
| Lumulse PEG 300 | Lambent Technologies | PEG-6 | Y | N | — |
| Lumulse PEG 400 | Lambent Technologies | PEG-8 Dimethicone | Y | N | — |
| Florasolvs PEG-10 Sunflower | Floratech Americas | PEG-10 Sunflower Glycerides | Y | N | — |
| Pluracare F68 | BASF | Poloxamer 188 | Y | N | — |
| Crodafos SG | Croda | PPG 5-Ceteth-10 Phosphate | Y | N | — |
| Procetyl AWS | Croda | PPG-5-Ceteth-20 | | | — |
| Incroquat 26 | Croda | Quaternium-26 | Y | Y | 4 |
| Silsense Q-plus | Noveon | Silicone Quaternium-8 | Y | Y | 4 |
| Dehyton MC | Cognis Corp. | Sodium Cocoamphoacetate | Y | N | — |

As shown above, derivatized dimethicones were capable of foaming the alcohol solution. Other conventional foaming agents, however, were not able to produce a foam.

As shown above, the best results were obtained using a dimethicone copolyol as the foaming agent. PEG-3 dimethicone, however, did not produce a foam. It is believed, however, that PEG-3 dimethicone may produce a foam when added in greater amounts or when added to an alcohol solution containing a lesser amount of alcohol.

As also shown above, various dimethicone copolyol esters were also capable of causing foam formation.

EXAMPLE 2

The following tests were conducted to determine if any synergistic effects may be noticed when various foaming agents were combined together in an alcohol solution.

In this example, a 70 percent ethanol solution was again tested using the same procedure as described in Example 1 above. Various different foaming agents were combined together and added to the ethanol solution. The following results were obtained:

| Foaming agent mixture by (by weight) in 70% Ethanol | Quality of Foam |
|---|---|
| 6% PEG-10 Dimethicone + 6% PEG-12 Dimethicone | 1 |
| 3% PEG-10 Dimethicone + 3% PEG-12 Dimethicone | 1 |
| 6% PEG-10 Dimethicone + 6% PEG-8 Dimethicone | 3 |
| 3% PEG-10 Dimethicone + 3% PEG-8 Dimethicone | 3 |
| 6% PEG-10 Dimethicone + 6% PEG-3 Dimethicone | no foam |
| 3% PEG-10 Dimethicone + 3% PEG-3 Dimethicone | no foam |
| 6% PEG-12 Dimethicone + 6% PPG-12 Dimethicone | no foam |
| 3% PEG-12 Dimethicone + 3% PPG-12 Dimethicone | no foam |
| 6% PEG-10 Dimethicone + 6% Dimethicone PEG-7 Cocoate | 1 |
| 3% PEG-10 Dimethicone + 3% Dimethicone PEG-7 Cocoate | 2 |
| 6% Quaternium-26 + 6% PEG-10 Dimethicone | 3 |
| 3% Quaternium-26 + 3% PEG-10 Dimethicone | 3 |

As shown above, some synergy was noticed when PEG-12 Dimethicone was mixed with PEG-10 Dimethicone.

EXAMPLE 3

The following is a formulation for producing foamable sanitizing compositions made in accordance with the present disclosure.

| Component | Active Wt. % | Function | Product Name | Source |
|---|---|---|---|---|
| PEG-10 Dimethicone | 1.50 | Foaming Agent | Silsurf Di-1010 | SilTech LLC |
| Denatured ethanol | 20-90% | Antimicrobial | — | Various |
| Meadowfoam Amidopropyldimethyl betaine | 0.40 | Foam Booster | Betafan M | Fanning Corp. |
| Betaine | 1.00 | Detackifier | Betafin BP-20 | Arch Chemicals |
| PEG-7 Glyceryl Cocoate | 1.00 | Emollient | Tegosoft GC | Degussa |
| Isopropyl alcohol | Up to 5.00 | Denaturant | — | Various |
| Fragrance | Up to 0.20 | Fragrance | — | — |
| Water | Balance | — | — | — |

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A foaming sanitizing product comprising:
   a dispensing container, the dispensing container including a non-aerosol pumping device;
   a foamable sanitizing composition contained within the dispensing container, the foamable sanitizing composition comprising an alcohol wherein the alcohol is present in the composition in an amount from about 30 percent to about 90 percent by weight of the composition, a derivatized dimethicone and an amphoteric or zwitterionic surfactant comprising surfactant molecules wherein at least 90% of the molecules have a hydrophobic carbon chain length of 18 carbon atoms or greater, water in an amount of at least 10% by weight; and
   wherein the pumping device of the dispensing container is configured to combine the sanitizing composition with air when dispensed from the container for producing a foam.

2. A foaming sanitizer product as defined in claim 1, wherein the pumping device comprises an air pump and a liquid pump in communication with an actuating head, and wherein displacing the actuating head manually causes the liquid pump to pump sanitizing composition and the air pump to pump air for mixing with the sanitizing composition and forming a foam that is dispensed from the container.

3. A foaming sanitizer product as defined in claim 1, wherein the derivatized dimethicone is present in the composition in an amount from about 0.5 percent to about 15 percent by weight of the composition.

4. A foaming sanitizer product as defined in claim 1, wherein the derivatized dimethicone comprises a dimethicone copolyol.

5. A foaming sanitizer product as defined in claim 4, wherein the dimethicone copolyol is linear.

6. A foaming sanitizer product as defined in claim 1, wherein the derivatized dimethicone contains a linear polyoxyethylene glycol dimethicone having from about 5 moles to about 20 moles of polyoxyethylene glycol.

7. A foaming sanitizer product as defined in claim 1, wherein the amphoteric or zwitterionic surfactant comprises meadowfoamamidopropyl betaine.

8. A foaming sanitizer product as defined in claim 1, wherein the alcohol is present in the composition in the amount of at least 20% by weight of the composition.

9. A foaming sanitizer product as defined in claim 8, wherein the alcohol comprises ethanol.

10. A foaming sanitizer product as defined in claim 8, wherein the amphoteric or zwitterionic surfactant is selected from the group consisting of canolamidopropyl betaine, behenamidopropyl betaine, behenyl betaine, dimer dilinoleamidopropyl betaine, almondamidopropyl betaine, cupuassuamidopropyl betaine, isostearamidopropyl betaine, oleamidopropyl betaine, oleylamidopropyl betaine, olivamidopropyl betaine, ricinoleamidopropyl betaine, sesamidopropyl betaine, soyamidopropyl betaine, stearamidopropyl betaine, steryl betaine, olivamidopropyl betaine, a surfactant of rapeseed oil, a surfactant of carnuba wax, a surfactant of candelilla wax, a surfactant of borage seed oil, a surfactant of linseed oil, a surfactant of castor oil, a surfactant of veronia oil, a surfactant of tung oil, a surfactant of jojoba oil, a surfactant of ongonkea oil, a surfactant of tall oil, and mixtures thereof.

11. A foaming sanitizer product as defined in claim 1, wherein the derivatized dimethicone comprises a mixture of polyoxyethylene glycol dimethicones having from about 5 moles to about 20 moles of polyoxyethylene glycol.

12. A foaming sanitizer product as defined in claim 1, wherein the derivatized dimethicone is selected from the group consisting of polyoxyethylene glycol dimethicone containing about 10 moles of polyoxyethylene glycol, polyoxyethylene glycol dimethicone containing about 12 moles of polyoxyethylene glycol or mixtures thereof, the polyoxyethylene glycol dimethicones being linear and being present in the composition in an amount from about 3 percent to about 15 percent by weight.

13. A foaming sanitizer product as defined in claim 1, wherein the composition further contains an organic sunscreen.

14. A foaming sanitizing product comprising:
  a dispensing container, the dispensing container including a non-aerosol pumping device;
  a foamable sanitizing composition contained within the dispensing container, the foamable sanitizing composition comprising an alcohol, the alcohol being present in the composition in an amount from about 30% to about 90% by weight, a derivatized dimethicone and an amphoteric or zwitterionic surfactant comprising surfactant molecules wherein at least 90% of the molecules have a hydrophobic carbon chain length of 18 carbon atoms or greater, and wherein the derivatized dimethicone contains a linear polyoxyethylene glycol dimethicone having from about 5 moles to about 20 moles of polyoxyethylene glycol, and wherein the amphoteric or zwitterionic surfactant is selected from the group consisting of meadowfoamamidopropyl betaine, canolamidopropyl betaine, behenamidopropyl betaine, behenyl betaine, dimer dilinoleamidopropyl betaine, almondamidopropyl betaine, cupuassuamidopropyl betaine, isostearamidopropyl betaine, oleamidopropyl betaine, oleylamidopropyl betaine, olivamidopropyl betaine, ricinoleamidopropyl betaine, sesamidopropyl betaine, soyamidopropyl betaine, stearamidopropyl betaine, steryl betaine, olivamidopropyl betaine, a surfactant of rapeseed oil, a surfactant of carnuba wax, a surfactant of candelilla wax, a surfactant of borage seed oil, a surfactant of linseed oil, a surfactant of castor oil, a surfactant of veronia oil, a surfactant of tung oil, a surfactant of jojoba oil, a surfactant of ongonkea oil, a surfactant of tall oil, or mixtures thereof, the derivatized dimethicone being present in the composition in an amount from about 0.5% to about 15% by weight, water in an amount of at least 10% by weight; and
  wherein the pumping device of the dispensing container is configured to combine the sanitizing composition with air when dispensed from the container for producing a foam.

* * * * *